United States Patent
Karandikar et al.

(10) Patent No.: US 9,487,759 B2
(45) Date of Patent: *Nov. 8, 2016

(54) PREPARATION OF STABILIZED CATALASE ENZYMES USING POLYVINYL ALCOHOL

(71) Applicant: Avent, Inc., Alpharetta, GA (US)

(72) Inventors: Bhalchandra M. Karandikar, Beaverton, OR (US); Sunita J. Macwana, Tigard, OR (US); Zhongju Liu Zhao, Sherwood, OR (US)

(73) Assignee: Avent, Inc., Alpharetta, GA (US)

(*) Notice: Subject to any disclaimer, the term of this patent is extended or adjusted under 35 U.S.C. 154(b) by 17 days.

This patent is subject to a terminal disclaimer.

(21) Appl. No.: 14/186,143

(22) Filed: Feb. 21, 2014

(65) Prior Publication Data

US 2014/0242056 A1 Aug. 28, 2014

Related U.S. Application Data

(60) Provisional application No. 61/769,395, filed on Feb. 26, 2013.

(51) Int. Cl.

| | | |
|---|---|---|
| *A61K 38/44* | (2006.01) | |
| *C02F 1/50* | (2006.01) | |
| *C02F 1/72* | (2006.01) | |
| *C02F 3/34* | (2006.01) | |
| *C12N 9/04* | (2006.01) | |
| *A61K 8/66* | (2006.01) | |
| *C12N 9/08* | (2006.01) | |
| *C12N 9/96* | (2006.01) | |
| *C12N 11/12* | (2006.01) | |
| *A61K 8/73* | (2006.01) | |
| *A61Q 19/00* | (2006.01) | |
| *A61K 8/81* | (2006.01) | |
| *A23L 3/3571* | (2006.01) | |
| *A23L 3/358* | (2006.01) | |
| *E21B 21/06* | (2006.01) | |
| *E21B 43/00* | (2006.01) | |

(52) U.S. Cl.
CPC ............ *C12N 9/0006* (2013.01); *A61K 8/66* (2013.01); *A61K 8/731* (2013.01); *A61K 8/8129* (2013.01); *A61Q 19/00* (2013.01); *C12N 9/0065* (2013.01); *C12N 9/96* (2013.01); *C12N 11/12* (2013.01); *C12Y 111/01006* (2013.01)

(58) Field of Classification Search
USPC .......................... 424/94.3; 435/188; 210/757
IPC ...... C12N 9/96; A61K 38/44; C02F 1/50,1/72, C02F 3/34; E21B 21/068, 21/06, 43/00; A23L 3/358

See application file for complete search history.

(56) References Cited

U.S. PATENT DOCUMENTS

| | | | |
|---|---|---|---|
| 2,689,203 A | 9/1954 | Lolli | |
| 3,006,815 A | 10/1961 | Scott | |
| 3,523,871 A * | 8/1970 | Yajima | C12N 9/96 435/188 |
| 3,933,588 A | 1/1976 | Dworschack et al. | |
| 3,954,974 A | 5/1976 | Herzog et al. | |
| 4,485,091 A | 11/1984 | Fitton | |
| 4,826,681 A | 5/1989 | Jacquet et al. | |
| 5,324,649 A * | 6/1994 | Arnold et al. | 435/187 |
| 5,380,764 A | 1/1995 | Herzog | |
| 5,792,090 A | 8/1998 | Ladin | |
| 6,045,813 A | 4/2000 | Ferguson et al. | |
| 6,485,950 B1 | 11/2002 | Kumar et al. | |
| 6,767,342 B1 | 7/2004 | Cantwell | |
| 7,160,553 B2 | 1/2007 | Gibbins et al. | |
| 8,148,316 B2 * | 4/2012 | DiCosimo et al. | 510/305 |
| 8,652,531 B2 | 2/2014 | Karandikar et al. | |
| 2001/0041188 A1 | 11/2001 | Gibbins et al. | |
| 2009/0074880 A1 | 3/2009 | Ladizinsky | |
| 2009/0202617 A1 | 8/2009 | Ward et al. | |
| 2009/0263539 A1* | 10/2009 | Herdt | A23L 3/3508 426/8 |
| 2009/0317478 A1 | 12/2009 | Han et al. | |
| 2010/0311668 A1* | 12/2010 | Farwick et al. | 514/18.8 |

FOREIGN PATENT DOCUMENTS

| | | |
|---|---|---|
| CA | 859115 A | 12/1970 |
| EP | 2 113 564 A1 | 11/2009 |
| FR | 2 666 812 A1 | 3/1992 |
| GB | 713720 A | 8/1954 |
| GB | 918056 A | 2/1963 |
| JP | 61-015685 A | 1/1986 |
| KR | 10-0804096 B | 2/2008 |
| WO | WO 9317721 A1 * 9/1993 | ............... A61L 2/00 |
| WO | WO 2009102770 A1 * 8/2009 | ............... C12N 9/98 |
| WO | WO2009152176 A2 * 12/2009 | ........... C07K 14/435 |
| WO | WO 2013/017995 A2 | 2/2013 |

OTHER PUBLICATIONS

Amo et al., 2002. Unique Presence of a Manganese Catalase in a Hyperthermophilic Archaeon, Pyrobaculum calidifontis VA1. Journal of Bacteriology, vol. 184, pp. 3305-3312.*

Sanjust et al., 1997. New Mercurated Resins for Covalent Immobilisation. European Polymer Journal, vol. 33, No. 4, pp. 549-551.*

Ayorinde. 2000.Analysis of some commercial polysorbate formulations using matrix-assisted laser desorption/ionization time-of-flight mass spectrometry. Rapid Communications in Mass Spectrometry, vol. 14, pp. 2116-2124.*

(Continued)

*Primary Examiner* — Debbie K Ware
*Assistant Examiner* — Kailash C Srivastava
(74) *Attorney, Agent, or Firm* — Dority & Manning, P.A.

(57) ABSTRACT

There is provided a method of producing a stabilized catalase enzyme. In the method, a substrate is thoroughly mixed with phosphate borate and catalase, rinsed with water and the solids dried. The dried solid may be mixed with polyvinyl alcohol and dried for further stabilization. The stabilized powder may be mixed with various skin solutions (lotions, ointments and the like). The catalase enzyme can catalyze the reaction of peroxide to oxygen.

8 Claims, No Drawings

(56) References Cited

OTHER PUBLICATIONS

Eberhardt et al. 2004. Immobilization of catalase from Aspergillus niger on inorganic and biopolymeric supports for H2O2 decomposition. Applied Catalysis B: Environmental, vol. 47, pp. 153-163.*

Mathur et al. (2005. Fenugreek and other lesser known legume galactomannan-polysaccharides: Scope for developments. Journal of Scientific & Industrial Research, vol. 64, pp. 475-481.*

Bergmeyer, H. 1965. Methods in Enzymatic Analysis, p. 893.*

Di Risio, Sabina et al., "Adsorption and Inactivation Behavior of Horseradish Peroxidase on Cellulosic Fiber Surfaces," Journal of Colloid and Interface Science, vol. 338, 2009, pp. 410-419.

Application Bulletin, "Emulsifier-Free Moisturizing Lotion (O/W)—Prepare a Cold-Processed, Oil-in-Water Lotion Using Avicel® PC 591 Microcrystalline Cellulose," FMC BioPolymer, Mastering the Art of Innovative Thinking, Issue No. 1, Jan. 2004, 2 pages.

* cited by examiner

PREPARATION OF STABILIZED CATALASE ENZYMES USING POLYVINYL ALCOHOL

This application claims priority to U.S. Provisional Application Ser. No. 61/769,395, filed on Feb. 26, 2013, which is incorporated herein in its entirety by reference thereto.

The present disclosure relates to a method of stabilizing catalase enzymes for longer term storage and stability until use. This disclosure also relates to the stabilized enzymes.

Oxygen is essential to sustaining life. Marine life utilize oxygen in dissolved form whereas land based species including humans utilize gaseous oxygen. The lack of oxygen or hypoxia is commonly experienced by people in their extremities (e.g. feet) as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Few formulations have focused on the direct delivery of oxygen to the skin.

Oxygen delivery to the skin has been examined for medical use, e.g. in treating of the compromised skin (wounds, inflammation and trauma) and more recently, intact skin. For example, Ladizinsky patented an oxygen generating wound dressing (U.S. Pat. No. 5,792,090). More recently, Gibbins et al. patented a method of making an oxygen generating foam dressing based on a polyacrylate polymer (U.S. Pat. No. 7,160,553). While the method of making an oxygen generating foam dressing is straightforward, the dressing itself suffers from a few drawbacks. For instance, the shelf life of the dressing is insufficient because oxygen from the dressing diffuses out of the foam cells over time. An alternative to the foam dressing in the form of an on-demand oxygen generating topical composition was proposed to overcome the limitation of the short shelf life (Ladizinsky US2009/0074880). In the '880 publication, a gel containing a catalyst and a peroxide in a separate reservoir, are brought together immediately before applying the mixture to the skin and covering it to maintain contact with the skin. Whether used for cosmetic applications or medical applications, oxygen generation is generally achieved though the catalytic decomposition of a peroxide, commonly hydrogen peroxide.

In any of the applications using catalyst and peroxide, a problem that has been found is that the catalyst can become inactivated during storage in a short period of time. Elevated temperatures accelerate this inactivation for many catalysts. For modern shipping and customer usage, it is important that the product be stable for a period of time sufficient to package, ship, market and sell it and to be stable in the user's home or other location. The stabilization of peroxide and/or a catalyst in a composition would be a step forward that would allow long term storage of the product. It would also be desirable if the product were stable at elevated temperatures commonly found in the shipping industry.

There is a need for a way of stabilizing a catalyst and/or peroxide for extended periods of time and at elevated temperatures. This would allow for the production, packaging, storage and shipping of a product without the product becoming deactivated before the customer was able to use it.

SUMMARY

There is provided a way of stabilizing a catalyst, particularly catalase, so that it may remain stable for an extended period of time. There is also provided a way of stabilizing a catalyst at elevated temperatures.

In the method, a substrate such as cellulose is thoroughly mixed with phosphate borate and catalase, rinsed with water and the solids dried. The dried solid may be mixed with polyvinyl alcohol and dried for further stabilization. The stabilized powder may be mixed with various skin solutions (lotions, ointments and the like). The catalase enzyme can catalyze the reaction of peroxide to oxygen.

DETAILED DESCRIPTION

Described below are methods of stabilizing catalase so that it may be stored without becoming deactivated. Catalase, an enzyme commonly produced by bacteria and fungi, can be used as a catalyst to decompose peroxide to oxygen. This decomposition is extremely rapid, but does depend on having a sufficient amount of catalase for a given amount of peroxide in order to be successful. Catalase can easily become inactivated over time so stabilizing the catalase can extent its useful lifetime and improve its commercial viability. Stabilization at higher temperatures is also important since temperatures experienced during shipping can be high enough to inactivate many catalysts.

The following procedure is a commonly accepted method of measuring catalase activity that is used to determine how well the catalase maintains its activity after stabilization and storage. After that are examples of the preparation of the disclosed stabilized catalase. Note that although the examples use microcrystalline cellulose as the substrate, any suitable substrate may be used, including ceramics and metals.

Analyzing for Catalase Activity

The activity of catalase enzyme is defined in International Units (IU). A solution or solid powder (in suspension) is defined to have an activity of one IU/ml or g if it can decompose 1 micromole of hydrogen peroxide per ml per minute at 25 C and pH 7. During the analysis for catalase activity, the hydrogen peroxide concentration is preferably maintained between 10 and 50 mM.

The analytical procedure for measuring catalase activity is straightforward and is known to those of ordinary skill in the enzyme industry. Briefly, following the addition of catalase solution of unknown concentration to the hydrogen peroxide solution, the peroxide absorbance value at 240 nm is monitored over time using a UV visible spectrophotometer. Since the optical density is linearly related to peroxide concentration, using the absorbance versus time data, the concentration of peroxide versus time data is obtained. Note that the molar extinction coefficient of hydrogen peroxide at 240 nm is 39.4 liter/mol-cm. From the kinetic data, the initial rate (at time 0) is obtained and used to calculate the catalase activity.

EXAMPLE 1

Comparative

Preparation of Cellulose Coated with Catalase with Poly Vinyl Alcohol (PVA) (CCP) Over-Coat (Non-Adsorption Method)

We report on a bench scale preparation method for cellulose catalase composite over-coated with PVA (hereafter referred to as CCP) that did not involve a prolonged adsorption step. The rationale was to learn if one could make robust CCP in a rapid manner; something that is commercially always desirable.

Briefly, microcrystalline cellulose powder (6.0 g, Avicel® PC 105 from FMC Biopolymer) was placed in a petri-dish. To the cellulose, a sufficient amount of catalase solution (Grade 1500 L, Activity: 50,000 IU/ml from BIO-CAT Inc. of Troy, Va.) was added for a target theoretical activity of CCP of ~10,000 IU/g. After swirling the slurry in the petri-dish for 15 minutes, the dish was placed in a vacuum chamber to remove moisture and dry the powder. Periodically, the weight of the petri-dish was checked. When no change in its weight was observed, the vacuum was discontinued. The dish was re-weighed and yielded ~5.98 g of CCP powder. The activity of CCP was found to be 2922 IU/g (See the general description of catalase activity measurement).

In the next step, sufficient quantity of 2.4% w/w PVA solution (PVA 98+% hydrolyzed, MW: 85K-124K from Sigma Aldrich) was added to the CCP corresponding to a PVA/cellulose mass ratio of 0.02. Once again, the slurry in the petri-dish was swirled for 15 minutes. Thereafter, the dish was returned to the vacuum chamber for removal of the solvent. When no change in the dish weight was observed (it took several hours), the vacuum was discontinued.

The dry CCP was scraped off the dish surface and transferred to a vial and stored at 4 C. The activity of CCP was measured to be 527 IU/g. Thus, following PVA coating and drying there was significant loss of activity of CCP.

To understand the aging effect, dry samples of CCP powder were maintained at 4 C, 25 C and 40 C for 1 week and then their activities were re-measured. At 25 C and 40 C, the values were 344 IU/g and 99 IU/g respectively registering 35% and 81% loss. At 4 C, the measured value of 441 IU/g indicated a loss of 16%. From the activity results, it is obvious that simply preparing CCP by simply blending respective ingredients and then drying the resulting mix did not yield a robust CCP prototype.

EXAMPLE 2

Preparation of Cellulose Powder Adsorbed with Catalase Over-Coated with PVA

Rather than merely mixing catalase, cellulose powder and PVA, here we describe a method of preparing microcrystalline cellulose powder adsorbed with catalase enzyme and then over-coated with a thin coating of PVA for protection (CCP-A). The method is identical to making CCP as disclosed in Example 1 with the exception of how the catalase is applied to the cellulose powder.

In an empty pre-weighed conical bottom polypropylene (PP) tube (from BD Falcon), a weighed quantity (0.5 g) of microcrystalline powder (Avicel® PC105) was added. This addition was followed by 4.5 ml phosphate borate buffer (0.05M, pH: 6.7) and 0.5 ml diluted catalase solution having an activity of 5000 U/ml. The diluted solution was prepared from a catalase stock solution (Grade 1500 L grade) having an activity of ~50,000 U/ml. The contents were briefly mixed on a vortex mixer and the tube was placed on a shaker set at 800 rpm for 24 hours.

After 24 h, the liquid from the tube was drained and the solids were rinsed three times using 5 ml de-ionized water each time. After each rinse, the liquid was discarded. After the third rinse, 1 ml of 1% w/w PVA solution was added to the wet cellulose solids in the tube and the contents were mixed uniformly on a vortex mixer. The resulting suspension was poured into a petri-dish. Any remaining cellulose in the tube was re-suspended by adding 2 ml de-ionized water and the suspension was transferred to the petri-dish.

The liquid in the petri-dish was allowed to air dry overnight at room temperature overnight inside a ventilated hood. The dry CCP-A powder was gently scraped of the dish surface with a blunt knife and weighed (0.4 g). The yield of CCP-A on cellulose weight basis was ~80%.

In this example a number of catalase activity measurements were carried out. First, the catalase activity for wet cellulose was measured (2282 U/g). Second, after drying, the activity of resulting CCP-A was measured at 1980 U/g. This is about a 13% loss in activity upon drying but this still was considered reasonable when compared with the results seen in Example 1.

EXAMPLE 3

Preparation of Skin Hydrator Blend with CCP-A 500 IU/g Activity

The objective of this test was to (i) prepare CCP-A sample, (ii) blend the CCP-A into Skin Hydrator lotion and (iii) subject the Skin Hydrator blend with CCP-A to thermal cycling (to simulate shipping transit) followed by accelerated age testing corresponding to a 2 years shelf life. The Skin Hydrator used herein is formula 1553-07 from Benchmark Laboratories of Fountain Valley, Calif., though it is believed that this procedure can be used with virtually any skin lotion, ointment or the like.

Preparation of CCP-A Powder

The following ingredients were added to a 15 ml PP conical tube and placed on a shaker at room temperature to effect adsorption of catalase on cellulose.

| Microcrystalline cellulose | 0.55 g |
|---|---|
| BIO-CAT 1500L | 1.67 ml |
| Phosphate buffer | 3.33 ml |

After the adsorption step, a procedure identical to that in Example 2 was followed to obtain CCP-A powder. In all, four batches were made and after pooling the batches yielded roughly 2.5 g of powder. Based on cellulose, the yield was >100% but this was the result of moisture, about 10%, that was present even after prolonged drying. Because the powder obtained was free flowing, it was used without further processing in the next step. The catalase activity of the pooled sample of CCP-A was measured at 5103 IU/g.

Preparation of Skin Hydrator Blend with CCP-A

Dry CCP-A powder (1.5 g) was blended into Skin Hydrator lotion (13.5 g) at 10% w/w loading to obtain starting catalase activity of ~500 IU/g in the sample. Because of the difficulty of measuring catalase activity in the lotion, the presence of catalase was confirmed indirectly by quantifying the decomposition of hydrogen peroxide after mixing it with O2 Reservoir lotion 1574-06 from Benchmark in 1:1 ratio. Freshly made Skin Hydrator lotion with catalase decomposed 100% peroxide in slightly more than 5 minutes. (The pass criterion was a minimum of 60% decomposition after 20 minutes.)

Thermal Cycling and Accelerated Aging of Skin Hydrator Lotion with CCP-A at 500 IU/g Activity Abbreviated thermal cycling was used because the cold condition (−20 C) was of no consequence as catalase is known to degrade at temperatures above 37 C. In the abbreviated thermal cycling, the lotion sample was aged at 40 C for 72 h followed by 55 C for 6 h. Next, the sample was placed in an oven set to 35 C and monitored for its efficacy to decompose peroxide over 16 weeks for accelerated aging. As a cosmetic industry norm, aging a product at 35 C for 16 weeks is considered a reasonable estimate of 2 years of real time shelf life. A second sample that served as control was maintained at room temperature (~25 C).

The table below shows the percentage peroxide decomposition values over 16 weeks. Note not all values are >60% which was set as the pass criterion. Nonetheless they are close to 60% within experimental error. Thus, we can conclude that Skin Hydrator lotion sample with CCP-A has demonstrated ability to withstand shipping transit and has met the two year shelf life criterion.

The results of peroxide decomposition for the entire duration are consistently above 60% thus handily passing the set criterion. Such outstanding stabilization effect on catalase in a very hostile environment has never been demonstrated before to our knowledge. Comparing the percentage decomposition results in Examples 3 and 4, it seems one would choose to have the starting catalase activity in a robust commercial Skin Hydrator lotion to be somewhere between 500 and 1000 IU/g for a 2 year shelf life. It is possible that the lotion sample in this Example could have exhibited the same efficacy for peroxide decomposition beyond 16 weeks, though it was not tested. With such long shelf life the present lotion prototype has already outperformed any known catalase containing product currently on the market.

As illustrated by Examples 2-4 above, there is herein provided a method of preparing stabilized microcrystalline cellulose through the steps of thoroughly mixing microcrystalline cellulose powder, phosphate borate and catalase enzyme to create a mixture having solids and liquid. The liquid is then drained from the mixture and the remaining solids are rinsed with water. Generally speaking, the ratio of cellulose to borate or catalase enzyme is between 1 and 10 and the ratio of borate to catalase enzyme is between 0.5 and 10. The resulting enzyme has an activity at 25 C between 500 IU/g and 1,000,000 IU/g.

The examples also show that a dry, flowable powder containing catalase may be made by the methods herein. Catalase is known to be difficult to stabilize in a dry form so this straight forward method provides an advancement to the art of catalyst stabilization.

TABLE 1

Accelerated Aging Test Results of Skin Hydrator Lotion Samples CCP-A @ 500 IU/g After Thermal Cycling @40 C./72 h and 55 C./6 h

| Sample ID | Temp | Start | Wk 1 | Wk 2 | Wk 3 | Wk 4 | Wk 5 | Wk 6 | Wk 7 | Wk 8 | Wk 9 | Wk 10 | Wk 11 | Wk 12 |
|---|---|---|---|---|---|---|---|---|---|---|---|---|---|---|
| 0191-66/500 IU | RT | 100% | 69% | 67% | 65% | 66% | 66% | ND | 62% | ND | 60% | ND | 65% | ND |
|  | 35 C. | 100% | 69% | 65% | 63% | 62% | 63% | ND | 56% | ND | 55% | ND | 59% | ND |

| Sample ID | Temp | Wk 13 | Wk 14 | Wk 15 | Wk 16 |
|---|---|---|---|---|---|
| 0191-66/500 IU | RT | 70% | ND | ND | 65% |
|  | 35 C. | 68% | ND | ND | 64% |

ND—Not determined

EXAMPLE 4

Preparation of Skin Hydrator Blend with CCP-A 1000 IU/g Activity

CCP-A was prepared in a manner similar to the Example 3 except for the following changes.

| | |
|---|---|
| Microcrystalline cellulose | 2.00 g |
| BIO-CAT 1500L | 2.00 ml |
| Phosphate buffer | 3.00 ml |

The resulting CCP-A powder had an enzymatic activity of 21,000 IU/g.

A blend of Skin Hydrator with adsorbed catalase was prepared by blending cellulose powder (1.0 g) into the base Skin Hydrator lotion (19.0 g) giving a starting catalase activity of ~1000 IU/g, twice the value for the samples in Example 3. The sample was subjected to thermal cycling as in Example 3 and then thermally aged at 35 C with an identical control sample maintained at 25 C. As before, each week, the sample efficacy to decompose peroxide was monitored for a period of 16 weeks. The results obtained as percentage decomposition values are listed in the table below.

TABLE 2

Accelerated Aging Test Results of Skin Hydrator Lotion Samples With CCP-A @ 1000 IU/g After Thermal Cycling @40 C./72 h and 55 C./6 h

| Sample ID | Temp | Start | Wk 1 | Wk 2 | Wk 3 | Wk 4 | Wk 5 | Wk 6 | Wk 7 | Wk 8 | Wk 9 | Wk 10 | Wk 11 | Wk 12 |
|---|---|---|---|---|---|---|---|---|---|---|---|---|---|---|
| 0191-68/1000 IU | RT | 100% | 90% | 85% | 81% | 86% | 85% | ND | 87% | ND | 83% | ND | 85% | ND |
|  | 35 C. | 100% | 90% | 80% | 79% | 76% | 76% | ND | 77% | ND | 80% | ND | 80% | ND |

| Sample ID | Temp | Wk 13 | Wk 14 | Wk 15 | Wk 16 |
|---|---|---|---|---|---|
| 0191-68/1000 IU | RT | 90% | ND | ND | 91% |
|  | 35 C. | 85% | ND | ND | 91% |

ND—Not determined

In addition to the stabilization of catalase as described herein, it has also been unexpectedly found that among the catalase derived from different organisms, the one derived from a fungus, *Aspergillus niger*, was most stable to thermal and chemical environments encountered. The catalase in buffered solution, in the adsorbed state on cellulose resisted degradation by heat or chemicals ingredients in cosmetic compositions and retained the necessary activity to produce compositions that survived rigorous shipping protocols and prolonged ageing under heat to simulate accelerated ageing.

Those ordinarily skilled in the art will recognize numerous strains of fungus are commercially available, though a desirable catalase source is fungus *Aspergillus niger*. It is important to note that this disclosure encompasses catalase derived from any source, including any fungal strain. The catalase molecules derived from *A. niger*, however, have been known to contain manganese atoms. Catalase may also be derived from genetically modified organisms where the catalase producing vector may be derived from *A. niger* or fungus in general and the host organisms in which the vector is inserted may be a fungus or another organism. Thus, in a broader aspect, the present disclosure encompasses catalase having manganese atom or atoms within its molecular structure regardless of which fungal or other organisms it is derived from. Catalase with manganese atoms in its molecular structure and having molecular weights <500,000 daltons are desirable.

The invention claimed is:

1. A method of preparing stabilized catalase enzyme comprising the steps of mixing a substrate comprising microcrystalline cellulose powder, a buffer, and catalase enzyme having a molecular weight of less than 500,000 Daltons to create a mixture including solids and liquid, draining the liquid from the mixture, rinsing the solids with water, thoroughly mixing the solids with polyvinyl alcohol, and drying the mixture to create a powder, wherein the stabilized catalase enzyme exhibits a decreased loss in catalase activity compared to catalase enzyme not mixed with the substrate and the polyvinyl alcohol, wherein the stabilized catalase enzyme has an activity at 25° C. between 500 IU/g and 1,000,000 IU/g, and wherein the stabilized catalase enzyme is stable for up to 16 weeks at 35° C. after thermal cycling of the stabilized catalase enzyme at 40° C. for 72 hours and 55° C. for 6 hours.

2. The method of claim 1, wherein the ratio of substrate to catalase enzyme is between 1 and 10.

3. The method of claim 1, wherein said catalase enzyme includes manganese atoms.

4. The method of claim 1, wherein said catalase enzyme is derived from fungus.

5. The method of claim 4, wherein the fungus is *Aspergillus niger*.

6. The method of claim 1, wherein the polyvinyl alcohol has a molecular weight between 85,000 and 124,000 Daltons.

7. The method of claim 1, wherein the stabilized catalase enzyme can decompose from above 60% to 91% hydrogen peroxide after thermal cycling when the ratio of the stabilized catalase enzyme to hydrogen peroxide is 1:1.

8. The method of claim 1, wherein the buffer comprises phosphate and borate.

* * * * *